US009969658B2

United States Patent
Pienaar et al.

(10) Patent No.: US 9,969,658 B2
(45) Date of Patent: May 15, 2018

(54) MATERIALS AND METHODS FOR PRODUCING ALKENES AND DERIVATIVES THEREOF

(71) Applicant: INVISTA North America S.a.r.l., Wilmington, DE (US)

(72) Inventors: Daniel Pienaar, Eaglescliffe (GB); Alex Conradie, Eaglescliffe (GB)

(73) Assignee: INVISTA NORTH AMERICA S.A.R.L., Wilmington, DE (US)

(*) Notice: Subject to any disclaimer, the term of this patent is extended or adjusted under 35 U.S.C. 154(b) by 0 days. days.

(21) Appl. No.: 15/094,923

(22) Filed: Apr. 8, 2016

(65) Prior Publication Data

US 2016/0297726 A1    Oct. 13, 2016

Related U.S. Application Data

(60) Provisional application No. 62/144,476, filed on Apr. 8, 2015.

(51) Int. Cl.

| C07C 1/24 | (2006.01) |
| B01D 3/00 | (2006.01) |
| B01D 3/34 | (2006.01) |
| B01D 3/38 | (2006.01) |
| C12P 7/42 | (2006.01) |
| B01D 15/10 | (2006.01) |
| B01D 15/42 | (2006.01) |

(52) U.S. Cl.
CPC ............... *C07C 1/24* (2013.01); *B01D 3/001* (2013.01); *B01D 3/009* (2013.01); *B01D 3/346* (2013.01); *B01D 3/38* (2013.01); *B01D 15/10* (2013.01); *B01D 15/426* (2013.01); *C12P 7/42* (2013.01); *Y02P 20/127* (2015.11)

(58) Field of Classification Search
None
See application file for complete search history.

(56) References Cited

U.S. PATENT DOCUMENTS

| 2,061,810 A | 11/1936 | Shiffler et al. |
| 3,751,402 A | 8/1973 | Broering |
| 5,849,971 A * | 12/1998 | Sakuth .................. B01D 3/009 203/29 |

(Continued)

FOREIGN PATENT DOCUMENTS

| WO | 2014/086780 A2 | 6/2014 |
| WO | 2016/164812 A1 | 10/2016 |

OTHER PUBLICATIONS

DSMZ, 81. Mineral Medium For Chemolithotrophic Growth (H-3), DSMZ, 2011.*

(Continued)

*Primary Examiner* — Philip Louie
(74) *Attorney, Agent, or Firm* — William J. Simmons; Thomas H. Jenkins

(57) ABSTRACT

The present disclosure relates to processes for production of alkene products from their alkene precursors, such as 3-hydroxyacid and alcohols, via either (1) high temperature reactive distillation with steam contact at optimal pH, (2) solvent extraction and Mulzer dehydration, (3) solid phase adsorption, desorption into an organic solvent and catalytic reaction and (4) high temperature reactive distillation with steam contact at optimal pH followed by catalytic conversion.

16 Claims, 9 Drawing Sheets

(56) References Cited

U.S. PATENT DOCUMENTS

| | | | |
|---|---|---|---|
| 8,367,886 B2* | 2/2013 | Gracey | C07C 1/24 |
| | | | 568/840 |
| 9,169,183 B1* | 10/2015 | Su | C07C 41/09 |
| 2008/0058572 A1* | 3/2008 | Fernandez | C07C 1/20 |
| | | | 585/640 |
| 2008/0132730 A1 | 6/2008 | Manzer et al. | |
| 2008/0220488 A1 | 9/2008 | D'Amore et al. | |
| 2008/0299630 A1* | 12/2008 | Maclennan | C12N 1/18 |
| | | | 435/161 |
| 2009/0048474 A1* | 2/2009 | Gracey | C07C 1/24 |
| | | | 585/315 |
| 2011/0172475 A1 | 7/2011 | Peters et al. | |
| 2014/0186913 A1 | 7/2014 | Botes et al. | |

OTHER PUBLICATIONS

Bianca et al., "Fermentative Production of Isobutene", Applied Microbial Biotechnology, vol. 93, 2012, pp. 1377-1387.

White, Claude WM., "Butadiene Production Process Overview", Chemico-Biological Interactions, vol. 166, 2007, pp. 10-14.

Whited et al., "Technology Update: Development of A Gas-Phase Bioprocess For Isoprene-Monomer Production Using Metabolic Pathway Engineering", Industrial Biotechnology, vol. 6, No. 3, Jun. 2010, pp. 152-163.

International Preliminary Report on Patentability received for PCT Patent Application No. PCT/US2016/026770, dated Oct. 19, 2017, 12 pages.

International Search Report and Written Opinion received for PCT Patent Application No. PCT/US2016/026770, dated Aug. 24, 2016, 16 pages.

\* cited by examiner

FIGURE 5

| Alkene precursor | Substrate initial concentration [ppm] | Alkene Product | GC-MS peak area | Headspace concentration measurement [ppm] |
|---|---|---|---|---|
| 3-hydroxy-3-methylpent-4-enoic acid | 500 | Isoprene | 3399586 | 652 |
|  | 1000 |  | 5952229 | 1138 |
| 3-hydroxy-4-methylpent-4-enoic acid | 1000 | Isoprene | 48704 | 14 |
| Mevalonic acid | 1000 | Isoprene | 179149 | 39 |
| 3-methyl-2-buten-1-ol | 500 | Isoprene | 496614 | 98 |
| 3-methyl-3-buten-1-ol | 500 | Isoprene |  | 5 |
| 2-methyl-3-buten-2-ol | 500 | Isoprene | 467038 | 94 |
| 3-hydroxy-3-methylbutyric acid | 500 | Isobutene | 123295 |  |

MATERIALS AND METHODS FOR PRODUCING ALKENES AND DERIVATIVES THEREOF

TECHNICAL FIELD

The present disclosure relates to for example methods producing alkene products. The present disclosure relates to materials and methods producing alkene products from 3-hydroxyacid, and alcohol precursors synthesized in fermentation, producing such alkenes in down-stream processing unit operations. For instance, the methods may be used to produce one or more of isoprene, butadiene and isobutene from alkene precursors. Alkene precursors may be converted to their respective alkenes via dehydrative decarboxylation or dehydration. Such vinyl group forming mechanisms may be promoted using, for example, (1) high temperature reactive distillation with steam contact at optimal pH, (2) solvent extraction followed by Mulzer dehydration, (3) solid phase adsorption and desorption into a solvent followed by catalytic conversion and (4) high temperature reactive distillation with steam contact at optimal pH followed by catalytic conversion. Given a reliance on petrochemical feedstocks, biotechnology offers an alternative approach to producing alkene precursors to isoprene, butadiene and isobutene.

BACKGROUND

Isoprene is an important monomer for the production of specialty elastomers including motor mounts/fittings, surgical gloves, rubber bands, golf balls and shoes. Styrene-isoprene-styrene block copolymers form a key component of hot-melt pressure-sensitive adhesive formulations and cis-poly-isoprene is utilised in the manufacture of tires (Whited et al., Industrial Biotechnology, 2010, 6(3), 152-163). Manufacturers of rubber goods depend on either imported natural rubber from the Brazilian rubber tree or petroleum-based synthetic rubber polymers (Whited et al., Industrial Biotechnology, 2010, 6(3), 152-163).

1,3-Butadiene (referred to herein as "butadiene") is an important monomer for the production of synthetic rubbers including styrene-butadiene-rubber (SBR), polybutadiene (PB), styrene-butadiene latex (SBL), acrylonitrile-butadiene-styrene resins (ABS), nitrile rubber, and adiponitrile. Adiponitrile is used in the manufacture of Nylon-6,6 (White, Chemico-Biological Interactions, 2007, 166, 10-14). Butadiene is typically produced as a co-product from the steam cracking process, distilled to a crude butadiene stream, and purified via extractive distillation (White, Chemico-Biological Interactions, 2007, 166, 10-14). On-purpose butadiene has been prepared among other methods by dehydrogenation of n-butane and n-butene (Houdry process); and oxidative dehydrogenation of n-butene (Oxo-D or O-X-D process) (White, Chemico-Biological Interactions, 2007, 166, 10-14). Industrially, 95% of global butadiene production is undertaken via the steam cracking process using petrochemical-based feedstocks such as naphtha. Production of on-purpose butadiene is not significant, given the high cost of production and low process yield (White, Chemico-Biological Interactions, 2007, 166, 10-14).

Isobutene is an important monomer in the manufacture of fuel additives, butyl rubber polymer, and antioxidants (Bianca et al., Appl. Microbiol Biotechnol., 2012, 93, 1377-1387). Manufacturers of goods using isobutene as feedstock depend on a number of petroleum-based sources, including (i) a C4 stream from a steam cracker separated from the butadiene, (ii) butene-butane fractions from a catalytic cracker and (iii) n-butane (from LPG) that is isomerized to isobutane and dehydrogenated to isobutene (Bianca et al., Appl. Microbiol Biotechnol., 2012, 93, 1377-1387).

Given a reliance on petrochemical feedstocks, biotechnology offers an alternative approach to producing alkene precursors to isoprene, butadiene and isobutene. Biocatalysis is the use of biological catalysts, such as enzymes or whole cells, to perform biochemical transformations of organic compounds.

Accordingly, against this background, it is clear that there is a need for sustainable methods for producing precursors to commodity alkenes, in particular isoprene, isobutene and butadiene, wherein the precursors are biocatalysis based.

SUMMARY

The present disclosure relates to the production of alkene products or derivatives thereof. The present disclosure relates to the production of alkene products from alkene precursors, such as 3-hydroxyacids and alcohols, derived from fermentation via dehydrative decarboxylation and dehydration respectively.

Accordingly, methods of converting alkene precursors are disclosed, wherein the alkene precursors are derived from fermentation, in downstream processing unit operations to their respective alkenes.

In one aspect, the present disclosure relates to methods comprising (1) high temperature reactive distillation with steam contact of the alkene precursor from the clarified fermentation broth, forming the alkene product in situ.

In another aspect, the disclosure relates to (1) solvent extraction of the alkene precursor from the clarified fermentation broth, followed by (2) a Mulzer dehydration reaction of the alkene precursor forming the respective alkene.

In another aspect, the present disclosure relates to (1) solid phase adsorption of the alkene precursor from the clarified fermentation broth and subsequent desorption into an organic solvent, followed by (2) catalytic reaction of the alkene precursor forming the respective alkene.

In another aspect, the present disclosure relates to (1) distillation or reactive distillation of the alkene precursor from the clarified fermentation broth, followed by (2) catalytic reaction of the alkene precursor forming the respective alkene.

The present disclosure further relates to methods for recovering the alkene product from one of the three methods described above, further subjecting the alkene product to membrane separation, adsorption or distillation or combinations thereof.

The present disclosure further relates to methods for recovering the alkene product from one of the three methods described above and further subjecting the alkene product to an optional polishing distillation step.

The present disclosure further relates to methods for recovering the alkene product from one of the three methods described above and further subjecting the alkene product to a condensation step.

The present disclosure further relates to a bio-derived product, bio-based product or fermentation-derived product, wherein said product is obtained from the process disclosed herein, and comprises:

i. a composition comprising at least one bio-derived, bio-based or fermentation-derived compound according to any process disclosed herein, or any one of FIGS. 1-9, or any combination thereof, ii. a bio-derived, bio-based or fermentation-derived polymer comprising the bio-derived, bio-based or fermentation-derived composition or compound of i., or any combination thereof, iii. a bio-derived, bio-based or fermentation-derived resin comprising the bio-derived, bio-based or fermentation-derived compound or bio-derived, bio-based or fermentation-derived composition of i. or any combination thereof, or the bio-derived, bio-based or fermentation-derived polymer of ii. or any combination thereof, iv. a molded substance obtained by molding the bio-derived, bio-based or fermentation-derived polymer of ii. or the bio-derived, bio-based or fermentation-derived resin of iii., or any combination thereof, v. a bio-derived, bio-based or fermentation-derived formulation comprising the bio-derived, bio-based or fermentation-derived composition of i., bio-derived, bio-based or fermentation-derived compound of i., bio-derived, bio-based or fermentation-derived polymer of ii., bio-derived, bio-based or fermentation-derived resin of iii., or bio-derived, bio-based or fermentation-derived molded substance of iv, or any combination thereof, or vi. a bio-derived, bio-based or fermentation-derived semi-solid or a non-semi-solid stream, comprising the bio-derived, bio-based or fermentation-derived composition of i., bio-derived, bin-based or fermentation-derived compound of i., bio-derived, bio-based or fermentation-derived polymer of ii., bio-derived, bio-based or fermentation-derived resin of iii., bio-derived, bio-based or fermentation-derived formulation of v., or bio-derived, bio-based or fermentation-derived molded substance of iv., or any combination thereof.

Unless otherwise defined, all technical and scientific terms used herein have the same meaning as commonly understood by one of ordinary skill in the art to which this present disclosure pertains. Although methods and materials similar or equivalent to those described herein can be used to practice the present disclosure, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the present disclosure are set forth in the accompanying drawings and the description below. Other features, objects, and advantages of the present disclosure will be apparent from the description and drawings, and from the claims.

DESCRIPTION OF DRAWINGS

FIG. 5 tabulates the conversion of alkene precursors to alkene products at elevated temperature and acidic pH in DSMZ media 81 as analyzed via GC-MS.

DETAILED DESCRIPTION

Before the present embodiments are described, it is to be understood that the present disclosure is not limited to the particular apparatus, adsorbents, methodologies or protocols described, as these may vary. It is also to be understood that the terminology used in the description is for the purpose of describing the particular versions or embodiments only, and is not intended to limit the scope of the present disclosure.

In accordance with the present disclosure, the materials and methods herein relate to the conversion of alkene precursors derived from fermentation to their respective alkene products. Alkene precursors include, but are not limited to; 3-hydroxyacids such as mevalonate, 3-methyl-3-hydroxybutyrate, 3-hydroxypent-4-enoate, 3-methyl-3-hydroxypent-4-enoate and 4-methyl-3-hydroxypent-4-enoate; primary alcohols such as 3-methyl-2-buten-1-ol and 3-methyl-3-buten-1-ol; secondary alcohols such as 3-buten-2-ol and 3-methyl-3-buten-2-ol; tertiary alcohols such as 2-methyl-3-buten-2-ol; all of which are referred to as alkene precursors herein. Alkene products include, but are not limited to, isoprene, butadiene or isobutene. The term "Mulzer dehydration" denotes herein, but is not limited to, reaction of a dehydrating agent, such as, for example, dimethyl-formamide-dimethylacetal, with an alkene precursor in an organic solvent, for example, a long chain ester such as hexyl acetate or octanyl acetate. The term "about" or "approximately" when used in connection with a specific value, means that acceptable deviations from that value are also encompassed but still provide substantially the same function as the specific value, High Temperature Reactive Distillation with Steam Contact Fermentation broth (see e.g., STREAM 1, FIG. 1) can be clarified by, for example, microfiltration or centrifugal separation or combination thereof. The separated biomass can be returned to fermentation (see e.g., STREAM 2, FIG. 1) or bled to waste treatment (see e.g., STREAM 4, FIG. 1) or combination thereof.

Figure 1:
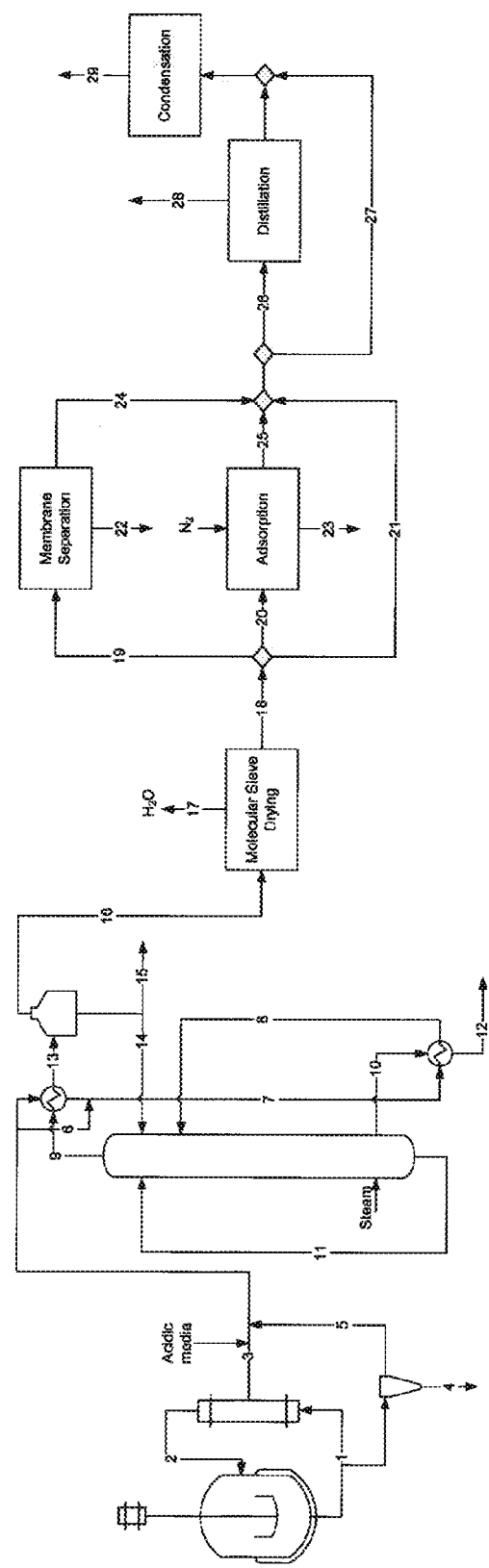
FIG. 1 is a schematic of an exemplary process flow diagram comprising high temperature reactive distillation with steam contact, converting an alkene precursor derived from fermentation to the respective alkene product.

The clarified fermentation broth originating from microfiltration (see e.g., STREAM 3, FIG. 1) and/or centrifugation (see e.g., STREAM 5, FIG. 1) can be fed to a high temperature reactive distillation unit with steam contact via a condenser with bypass (see e.g., STREAM 6, FIG. 1) and/or a recovery heat exchanger (see e.g., STREAM 7, FIG. 1). For 3-hydroxyacid alkene precursors, the pH of the clarified broth can be adjusted to approximately 3 using an acidic media comprising concentrated fermentation media pH adjusted with sulphuric acid or phosphoric acid (see e.g., STREAM 3, FIG. 1). An alkene polymerisation inhibitor can also be added to the feed.

The preheated clarified fermentation broth can be fed to a packed column (see e.g., STREAM 8, FIG. 1) operated at approximately 150° C. by contacting the feed directly with high pressure steam or indirectly with high pressure steam via a reboiler.

The column bottoms hold-up can be recycled (see e.g., STREAM 11, FIG. 1) to the feed position, whilst bottoms withdrawal (see e.g., STREAM 10, FIG. 1) is via a recovery heat exchanger. The feed rate to the reactive distillation unit (see e.g., STREAM 8, FIG. 1) is controlled to minimise the concentration of at least one alkene precursor in the bottoms outflow (see e.g., STREAM 12, FIG. 1).

The high temperature reactive distillation with steam contact increases the reaction rate for the dehydrative decarboxylation of 3-hydroxyacids, such as mevalonate, 3-methyl-3-hydroxybutyrate, 3-hydroxypent-4-enoate, 3-methyl-3-hydroxypent-4-enoate and 4-methyl-3-hydroxypent-4-enoate and the dehydration of such as 3-methyl-2-buten-1-ol, 3-methyl-3-buten-1-ol, 3-buten-2-ol, 3-methyl-3-buten-2-ol and 2-methyl-3-buten-2-ol to their respective alkene products.

The alkene product mixture is withdrawn as top product from the reactive distillation unit (see e.g., STREAM 9, FIG. 1) and the top product can be partially condensed, retaining the alkene product mixture in the vapour phase (see e.g., STREAM 13, FIG. 1).

The condensed fraction of the top product can be returned to the column's feed position (see e.g., STREAM 14, FIG. 1), recycling, for example, unreacted alkene precursors such as azeotropic alcohols to the reactive distillation unit. The top product recycle (see e.g., STREAM 14, FIG. 1) flow rate maintains a low concentration of unreacted alkene precursors in the top product outflow (see e.g., STREAM 15, FIG. 1).

The water saturated alkene product mixture (see e.g., STREAM 16, FIG. 1) can be fed to a drying unit operation, packed with an adsorbent such as a molecular sieve, removing water (see e.g., STREAM 17, FIG. 1) to a low dew point of, for example, −20° C. and produce a dry alkene product mixture.

The dry alkene product mixture (see e.g., STREAM 18, FIG. 1) can be fed to an adsorption unit operation packed with an adsorbent selective for alkenes such as a zeolite. Volatile organic by-products, such as alcohols and aldehydes, originating from the clarified fermentation broth are removed in the adsorption flow-through (see e.g., STREAM 23, FIG. 1), whilst the alkene product is desorbed using, for example, nitrogen to produce a desorbed alkene product (see e.g., STEAM 25, FIG. 1). The desorbed alkene product can be fed to a polishing distillation unit operation optionally involving a pre-condenser via compression or chilling (see e.g., STREAM 26, FIG. 1), followed by a condensation unit operation producing the high purity alkene product (see e.g., STREAM 29, FIG. 1). The desorbed alkene product can also be fed directly to a condensation unit operation (see e.g., STREAM 27, FIG. 1), producing the high purity alkene product (see e.g., STREAM 29, FIG. 1). Separation of the alkene from any permanent gases, such as nitrogen, can be achieved by, for example, complete condensation of the desorbed alkene product.

The dry alkene product (see e.g., STREAM 18, FIG. 1) can be fed to a membrane separation unit operation using a membrane selective for alkenes such as a zeolite membrane. Volatile organic by-products, such as alcohols and aldehydes, originating from the clarified fermentation broth are removed via the retentate bleed (see e.g., STREAM 22, FIG. 1), whilst the alkene product is collected as permeate (see e.g., STREAM 24, FIG. 1). The permeate containing the alkene product can be fed to a polishing distillation unit operation optionally involving a pre-condenser via compression or chilling (see e.g., STREAM 26, FIG. 1) to remove impurities (see e.g., STREAM 28, FIG. 1), followed by a condensation unit operation producing the high purity alkene product (see e.g., STREAM 29, FIG. 1). The permeate containing the alkene product can also be fed directly to a condensation unit operation (see e.g., STREAM 27, FIG. 1), producing the high purity alkene product (see e.g., STREAM 29, FIG. 1).

The dry alkene product (see e.g., STREAM 18, FIG. 1) can be fed directly to a distillation unit operation (see e.g., STREAM 21, FIG. 1), followed by a condensation unit operation producing the high purity alkene product (see e.g., STREAM 29, FIG. 1).

Solvent Extraction and Mulzer Dehydration Reaction

Figure 2:
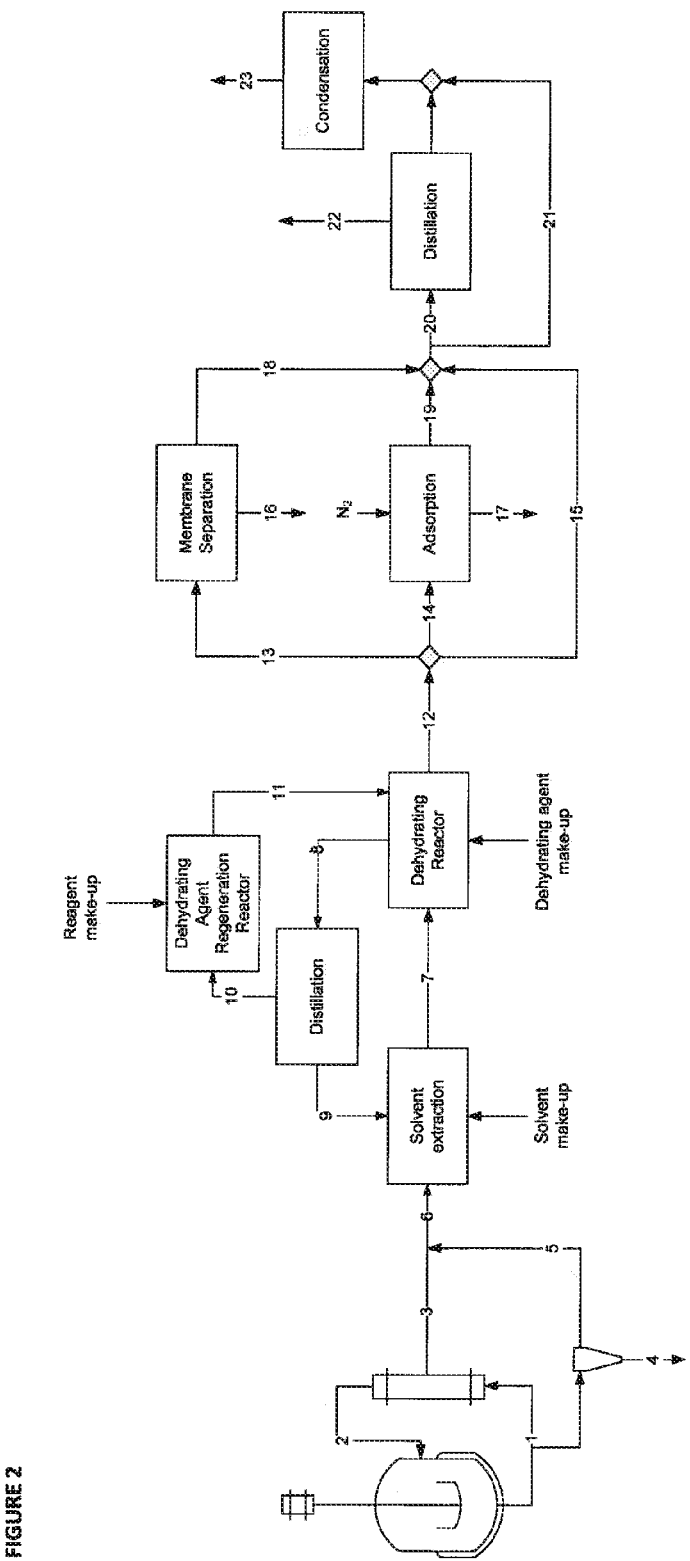
FIG. 2 is a schematic of an exemplary process flow diagram comprising solvent extraction and Mulzer dehydration, converting an alkene precursor derived from fermentation to the respective alkene product.

Fermentation broth (see e.g., STREAM 1, FIG. 2) can be clarified by, for example, microfiltration or centrifugal separation or combination thereof. The separated biomass can be returned to fermentation (see e.g., STREAM 2, FIG. 2) or bled to waste treatment (see e.g., STREAM 4, FIG. 2) or a combination thereof. The clarified fermentation broth originating from microfiltration (see e.g., STREAM 3, FIG. 2) and/or centrifugation (see e.g., STREAM 5, FIG. 2) can be fed to a solvent extraction unit operation (see e.g., STREAM 6, FIG. 2), contacting a solvent that has a high selectively for 3-hydroxyacids or alcohols, low miscibility in water and promotes Mulzer dehydration reactions, for example, a long chain ester such as hexyl acetate or octanyl acetate; to produce a solvent extracted alkene precursor (see e.g., STREAM 7, FIG. 2). In one aspect, the clarified fermentation broth is extracted with a solvent comprising a long chain ester such as hexyl acetate and octanyl acetate.

The solvent extracted alkene precursor mixture is fed (see e.g., STREAM 7, FIG. 2) to a dehydration reactor, contacting the solvent extracted alkene precursor with a Mulzer dehydrating agent such as dimethyl-formamide-dimethylacetal, forming an alkene product mixture. The dehydrating reactor's solvent phase can be fed to a distillation train (see e.g., STREAM 8, FIG. 2), recycling the solvent to the solvent extraction unit operation (see e.g., STREAM 9, FIG. 2) and feeding the Mulzer dehydrating agent to a regeneration reactor (see e.g., STREAM 10, FIG. 2). The regenerated Mulzer dehydrating agent can be recycled to the dehydrating reactor (see e.g., STREAM 11, FIG. 2).

The alkene product mixture in the vapour phase of the dehydrating reactor (see e.g., STREAM 12, FIG. 2) can be fed (see e.g., STREAM 14, FIG. 2) to an adsorption unit operation packed with an adsorbent selective for alkenes such as a zeolite. Volatile organic by-products, such as alcohols and aldehydes, originating from the clarified fermentation broth are removed in the adsorption flow-through (see e.g., STREAM 17, FIG. 2), whilst the alkene product is adsorbed and subsequently desorbed using, for example, nitrogen to produce a desorbed alkene product (see e.g., STEAM 19, FIG. 2). The desorbed alkene product can be fed to a polishing distillation unit operation optionally involving a pre-condenser via compression or chilling (see e.g., STREAM 20, FIG. 2) to remove impurities (see e.g., STREAM 22, FIG. 2), followed by a condensation unit operation producing the high purity alkene product (see e.g., STREAM 23, FIG. 2). The desorbed alkene product can also be fed directly to a condensation unit operation (see e.g., STREAM 21, FIG. 2), producing the high purity alkene product (see e.g., STREAM 23, FIG. 2).

The alkene product mixture in the vapour phase of the dehydrating reactor (see e.g., STREAM 12, FIG. 2) can be fed (see e.g., STREAM 13, FIG. 2) to a membrane separation unit operation using a membrane selective for alkenes such as a zeolite membrane. Volatile organic by-products, such as alcohols and aldehydes, originating from the clarified fermentation broth are removed via the retentate bleed (see e.g., STREAM 16, FIG. 2), whilst the alkene product is collected as permeate (see e.g., STREAM 18, FIG. 2). The permeate containing the alkene product can be fed to a polishing distillation unit operation optionally involving a pre-condenser via compression or chilling (see e.g., STREAM 20, FIG. 2), followed by a condensation unit operation producing the high purity alkene product (see e.g., STREAM 23, FIG. 2). The permeate containing the alkene product can also be fed directly to a condensation unit operation (see e.g., STREAM 21, FIG. 2), producing the high purity alkene product (see e.g., STREAM 23, FIG. 2).

Solid Phase Adsorption, Desorption into Organic Solvent and Catalytic Reaction

Fermentation broth (see e.g., STREAM 1, FIG. 3) can be clarified by, for example, microfiltration or centrifugal separation or combination thereof. The separated biomass can be returned to fermentation (see e.g., STREAM 2, FIG. 3) or bled to waste treatment (see e.g., STREAM 4, FIG. 3) or combination thereof. The clarified fermentation broth originating from microfiltration (see e.g., STREAM 3, FIG. 3) and/or centrifugation (see e.g., STREAM 5, FIG. 3) can be fed to an adsorption unit operation (see e.g., STREAM 6, FIG. 3), contacting a solid phase adsorbent that has high selectively for 3-hydroxyacids, such as an anionic exchange resin, or alcohols, such as a weakly polar polystyrene macroporous resin or a zeolite. The adsorbed precursor is desorbed into (1) high concentration aqueous ammonia or ammonium (bi)carbonate or (2) an organic solvent such as methanol.

Figure 3:
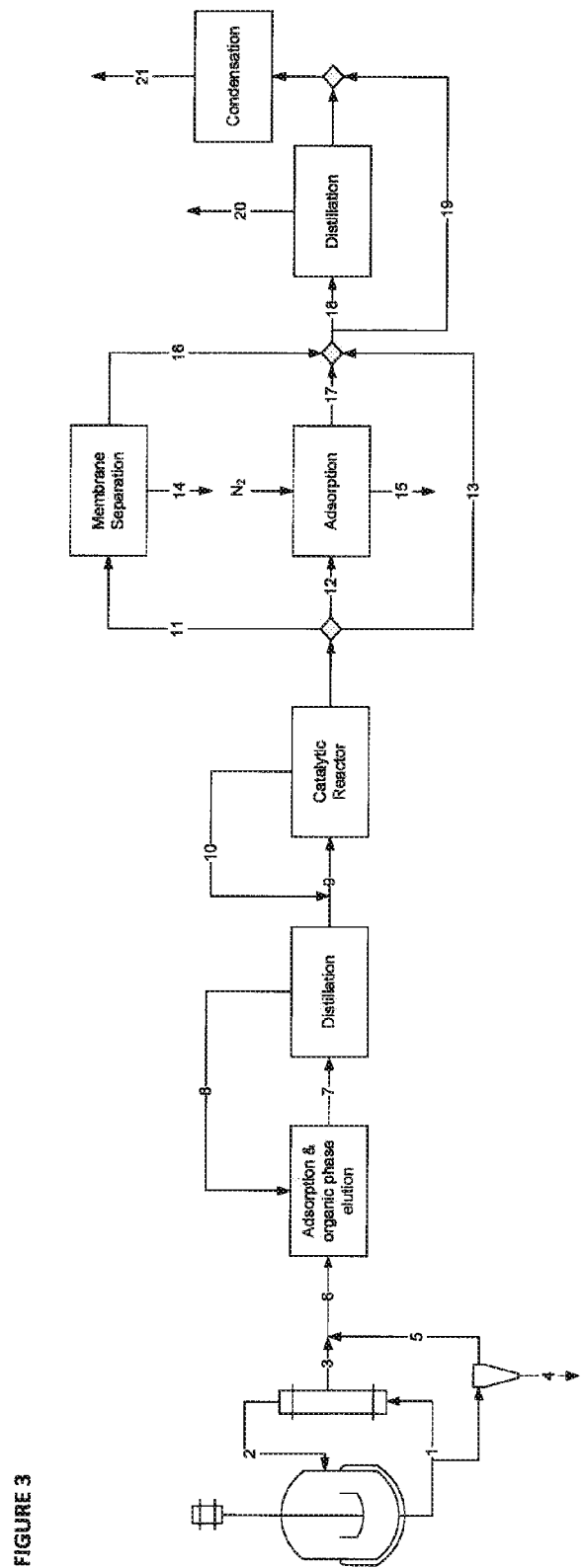
FIG. 3 is a schematic of an exemplary process flow diagram comprising adsorption of the alkene precursor from the clarified fermentation broth, followed by desorption into an organic solvent and thereafter converted via catalytic reaction to the respective alkene.

The desorbed alkene precursor is fed (see e.g., STREAM 7, FIG. 3) to a distillation step, comprising one or more distillation units, purifying the desorbed alkene precursor as a suitable feed to a catalytic reactor (see e.g., STREAM 9, FIG. 3). The desorbent recovered during distillation can be recycled to the adsorption unit operation (see e.g., STREAM 8, FIG. 3).

The catalytic reactor converts the at least one alkene precursor (see e.g., STREAM 9, FIG. 3) to the alkene product mixture using (1) a dehydrating or dehydrative decarboxylating catalyst such as thorium oxide at high temperature or (2) high temperature in the absence of a catalyst. Unreacted alkene precursor can be recycled to the catalytic reactor feed (see e.g., STREAM 10, FIG. 3).

The alkene product mixture in the vapour phase of the catalytic reactor can be fed (see e.g., STREAM 12, FIG. 3) to an adsorption unit operation packed with an adsorbent selective for alkenes such as a zeolite. Volatile organic by-products are removed in the adsorption flow-through (see e.g., STREAM 15, FIG. 3), whilst the alkene product is adsorbed and subsequently desorbed using, for example, nitrogen to produce a desorbed alkene product (see e.g., STEAM 17, FIG. 3). The desorbed alkene product can be fed to a polishing distillation unit operation optionally involving a pre-condenser via compression or chilling (see e.g., STREAM 18, FIG. 3) to remove impurities (see e.g., STREAM 20, FIG. 3), followed by a condensation unit operation producing the high purity alkene product (see e.g., STREAM 21, FIG. 3). The desorbed alkene product can also be fed directly to a condensation unit operation (see e.g., STREAM 19, FIG. 3), producing the high purity alkene product (see e.g., STREAM 21, FIG. 3).

The alkene product mixture in the vapour phase of the catalytic reactor can be fed (see e.g., STREAM 11, FIG. 3) to a membrane separation unit operation using a membrane selective for alkenes such as a zeolite membrane. Volatile organic by-products can be removed via the retentate bleed (see e.g., STREAM 14, FIG. 3), whilst the alkene product is collected as permeate (see e.g., STREAM 16, FIG. 3). The permeate containing the alkene product can be fed to a polishing distillation unit operation optionally involving a pre-condenser via compression or chilling (see e.g., STREAM 18, FIG. 3) to remove impurities (see e.g., STREAM 20, FIG. 3), followed by a condensation unit operation producing the high purity alkene product (see e.g., STREAM 21, FIG. 3). The permeate containing the alkene product (see e.g., STREAM 16, FIG. 3) can also be fed directly to a condensation unit operation (see e.g., STREAM 19, FIG. 3), producing the high purity alkene product (see e.g., STREAM 21, FIG. 3).

High Temperature Reactive Distillation with Steam Contact and Catalytic Reaction Fermentation broth (see e.g., STREAM 1, FIG. 4) can be clarified by, for example, microfiltration or centrifugal separation or combination thereof. The separated biomass can be returned to fermentation (see e.g., STREAM 2, FIG. 4) or bled to waste treatment (see e.g., STREAM 4, FIG. 4) or combination thereof.

Figure 4:
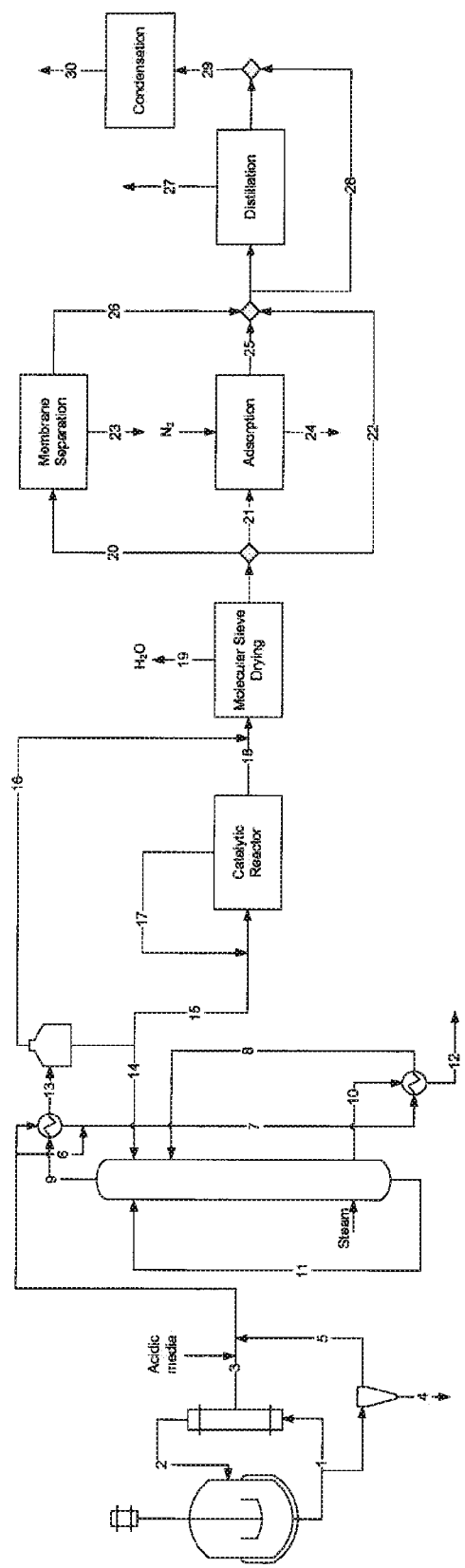
FIG. 4 is a schematic of an exemplary process flow diagram comprising high temperature reactive distillation with steam contact of the alkene precursor, followed by catalytic conversion to the respective alkene product.

The clarified fermentation broth originating from microfiltration (see e.g., STREAM 3, FIG. 4) and/or centrifugation (see e.g., STREAM 5, FIG. 4) can be fed to a high temperature reactive distillation unit with steam contact via a condenser with bypass (see e.g., STREAM 6, FIG. 4) and/or a recovery heat exchanger (see e.g., STREAM 7, FIG. 4). For 3-hydroxyacid alkene precursors, the pH of the clarified broth can be adjusted to approximately 3 using an acidic media comprising concentrated fermentation media pH adjusted with sulphuric acid or phosphoric acid (see e.g., STREAM 3, FIG. 4). An alkene polymerisation inhibitor can also be added to the feed.

The preheated clarified fermentation broth can be fed to a packed column (see e.g., STREAM 8, FIG. 4) operated at approximately 150° C. by contacting the feed directly with high pressure steam or indirectly with high pressure steam via a reboiler.

The column bottoms hold-up can be recycled (see e.g., STREAM 11, FIG. 4) to the feed position, whilst bottoms withdrawal (see e.g., STREAM 10, FIG. 4) is via a recovery heat exchanger. The feed rate to the reactive distillation unit (see e.g., STREAM 8, FIG. 4) is controlled to minimise the concentration of at least one alkene precursor in the bottoms outflow (see e.g., STREAM 12, FIG. 4).

The high temperature reactive distillation with steam contact increases the reaction rate for the dehydrative decarboxylation of 3-hydroxyacids, such as mevalonate forming either 3-methyl-2-buten-1-ol and/or 3-methyl-3-buten-1-ol. The high temperature distillation recovers azeotropic alcohols such as 3-methyl-2-buten-1-ol, 3-methyl-3-buten-1-ol, 3-buten-2-ol, 3-methyl-3-buten-2-ol and 2-methyl-3-buten-2-ol to the distillate product (see e.g., STREAM 9, FIG. 4).

The alkene/alcohol product mixture is withdrawn as top product from the reactive distillation unit (see e.g., STREAM 9, FIG. 4) and the top product can be partially condensed, retaining the alkene product mixture in the vapour phase (see e.g., STREAM 13, FIG. 4).

The condensed fraction of the top product can be returned to the column's feed position (see e.g., STREAM 14, FIG. 4), recycling, for example, unreacted alkene precursors such as azeotropic alcohols to the reactive distillation unit. The top product recycle (see e.g., STREAM 14, FIG. 4) flow rate maintains an azeotropic concentration of unreacted alkene precursors in the top product outflow (see e.g., STREAM 15, FIG. 4). The azeotropic concentration of unreacted alkene precursors (see e.g., STREAM 15, FIG. 4) can be fed to a catalytic reactor. The catalytic reactor converts the at least one alkene precursor (see e.g., STREAM 15, FIG. 4) to the alkene product mixture using (1) a dehydrating catalyst such as thorium oxide at high temperature or (2) high temperature in the absence of a catalyst. Unreacted alkene precursor can be recycled to the catalytic reactor feed (see e.g., STREAM 17, FIG. 4).

The water saturated alkene product mixture (see e.g., STREAM 16, FIG. 4) and the catalytic reactor product (see e.g., STREAM 18, FIG. 4) can be fed to a drying unit operation, packed with an adsorbent such as a molecular sieve, removing water (see e.g., STREAM 19, FIG. 4) to a low dew point of, for example, −20° C. and produce a dry alkene product mixture.

The dry alkene product mixture (see e.g., STREAM 21, FIG. 4) can be fed to an adsorption unit operation packed with an adsorbent selective for alkenes such as a zeolite. Volatile organic by-products, such as alcohols and aldehydes, originating from the clarified fermentation broth are removed in the adsorption flow-through (see e.g., STREAM 24, FIG. 4), whilst the alkene product is desorbed using, for example, nitrogen to produce a desorbed alkene product (see e.g., STEAM 25, FIG. 4). The desorbed alkene product can be fed to a polishing distillation unit operation optionally involving a pre-condenser via compression or chilling (see e.g., STREAM 25, FIG. 4), followed by a condensation unit operation producing the high purity alkene product (see e.g., STREAM 30, FIG. 4). The desorbed alkene product can also be fed directly to a condensation unit operation (see e.g., STREAM 28, FIG. 4), producing the high purity alkene product (see e.g., STREAM 30, FIG. 4). Separation of the alkene from any permanent gases, such as nitrogen, can be achieved by, for example, complete condensation of the desorbed alkene product.

The dry alkene product (see e.g., STREAM 20, FIG. 4) can be fed to a membrane separation unit operation using a membrane selective for alkenes such as a zeolite membrane. Volatile organic by-products, such as alcohols and aldehydes, originating from the clarified fermentation broth are removed via the retentate bleed (see e.g., STREAM 23, FIG. 4), whilst the alkene product is collected as permeate (see e.g., STREAM 26, FIG. 4). The permeate containing the alkene product can be fed to a polishing distillation unit operation optionally involving a pre-condenser via compression or chilling (see e.g., STREAM 26, FIG. 4) to remove impurities (see e.g., STREAM 27, FIG. 4), followed by a condensation unit operation producing the high purity alkene product (see e.g., STREAM 30, FIG. 4). The permeate containing the alkene product can also be fed directly to a condensation unit operation (see e.g., STREAM 28, FIG. 4), producing the high purity alkene product (see e.g., STREAM 30, FIG. 4).

The dry alkene product can be fed directly to a distillation unit operation (see e.g., STREAM 22, FIG. 4), followed by a condensation unit operation producing the high purity alkene product (see e.g., STREAM 30, FIG. 4).

EXAMPLES

Example 1

Conversion of Alkene Recursors Dissolved in Fermentation Media to Alkene Nets Via Residence Time at Elevated Temperature at Optimal pH DSMZ fermentation medium 81 was adjusted to pH=3.0 using concentrated phosphoric acid. The acidic fermentation medium was pipetted into GC vials and preheated to 95 [° C.]. Each of the alkene precursors tabulated in FIG. 5 was pipetted into the GC vials individually in duplicate to either a final concentration of 500 [ppm] or 1000 [ppm] as outlined in FIG. 5. Each GC vial was immediately crimped and incubated at 95 [° C.] for 30 [min]. The vials were cooled to room temperature prior to GC-MS analysis.

For isoprene analysis via GC-MS, a standard curve was generated using an isoprene in methanol analytical standard dispensed into the acidic fermentation media, measuring the isoprene concentration in the headspace of the vials. Isobutene formation was confirmed via an analytical standard prepared by saturating isobutene gas in water, measuring the isobutene concentration in the headspace of the standard.

FIG. 5 outlines the conversion of each alkene precursor to its respective alkene product. The alkene precursors 3-hydroxy-3-methylpent-4-enoic acid and 3-hydroxy-3-methylbutyric acid were converted to isoprene and isobutene respectively at high conversion. The conversion of 3-hydroxy-4-methylpent-4-enoic acid was detected.

The alkene precursors 3-methyl-2-buten-1-ol and 2-methyl-3-buten-2-ol were converted to isoprene at moderate conversion, whilst conversion of 3-methyl-3-buten-1-ol to isoprene was detected.

Mevalonic acid conversion to isoprene in DSMZ-81 fermentation media at pH≤3.0 was detected alongside a peak predicted by GC-MS to be either 3-methyl-3-buten-1-ol or 3-methyl-2-buten-1-ol.

The results presented in FIG. 5 demonstrate that 3-hydroxyacids alkene precursors, such as 3-hydroxy-3-methylpent-4-enoic acid, 3-hydroxy-3-methylbutyric acid, 3-hydroxy-4-methylpent-4-enoic acid and mevalonic acid, can be converted in DSMZ-81 fermentation media to their respective alkene products at elevated temperature and acidic pH.

The results presented in FIG. 5 demonstrate that alcohol precursors to alkene products, such as 3-methyl-2-buten-1-ol, 2-methyl-3-buten-2-ol and 3-methyl-3-buten-1-ol, can be converted in DSMZ-81 fermentation media to their respective alkene products at elevated temperature and acidic pH.

The results presented in FIG. 5 demonstrate that mevalonic acid can be converted in DSMZ-81 fermentation media to isoprene and 3-methyl-3-buten-1-ol/3-methyl-2-buten-1-ol (predicted) respectively at elevated temperature and acidic pH.

Example 2

Conversion of 3-hydroxy-3-methylpent-4-enoic Acid Dissolved in Fermentation Media to Isoprene via Reactive Distillation with Steam Contact at Optimal pH A large scale laboratory reactive distillation unit with a temperature controlled flash drum was designed to operate at elevated pressure and temperature to demonstrate the continuous conversion of 3-hydroxyacid precursors to their respective alkene products. The flash drum was fitted with a knock-out after-cooler fed with chilled water at approximately 10 [° C.]. The flash drum was charged with water and temperature controlled to 20 [° C.]. The vapour product from the distillation unit was bubbled through the water charge and a constant flow of $N_2$ at 0.3 [SL/min] was introduced as carrier and stripping gas. The uncondensed vapour product from the flash drum was fed to a Raman Spectrometer, calibrated with a 0.5 [%] (v/v) 1,3-butadiene calibration cylinder as double bond reference gas to analyse for the concentration of double bonds in the vapour product from the flash drum.

Figure 6:
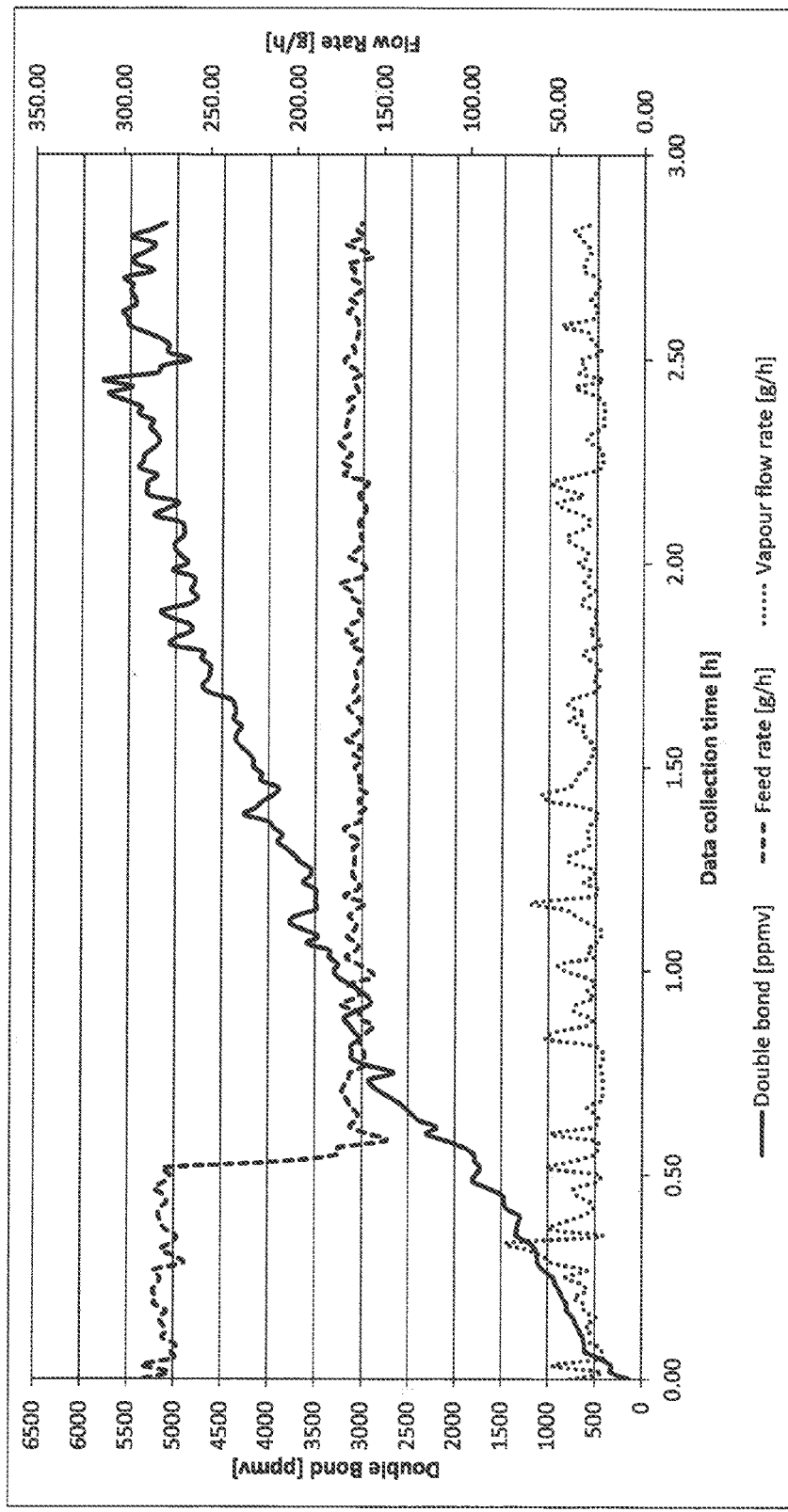
FIG. 6 graphs the continuous conversion of 3-hydroxy-3-methylpent-4-enoic acid to isoprene at elevated temperature and acidic pH in DSMZ media 81 in a reactive distillation unit operation with steam contact, showing the approach to steady state conversion alongside feed rate and total vapor product flow rate.
Figure 7:
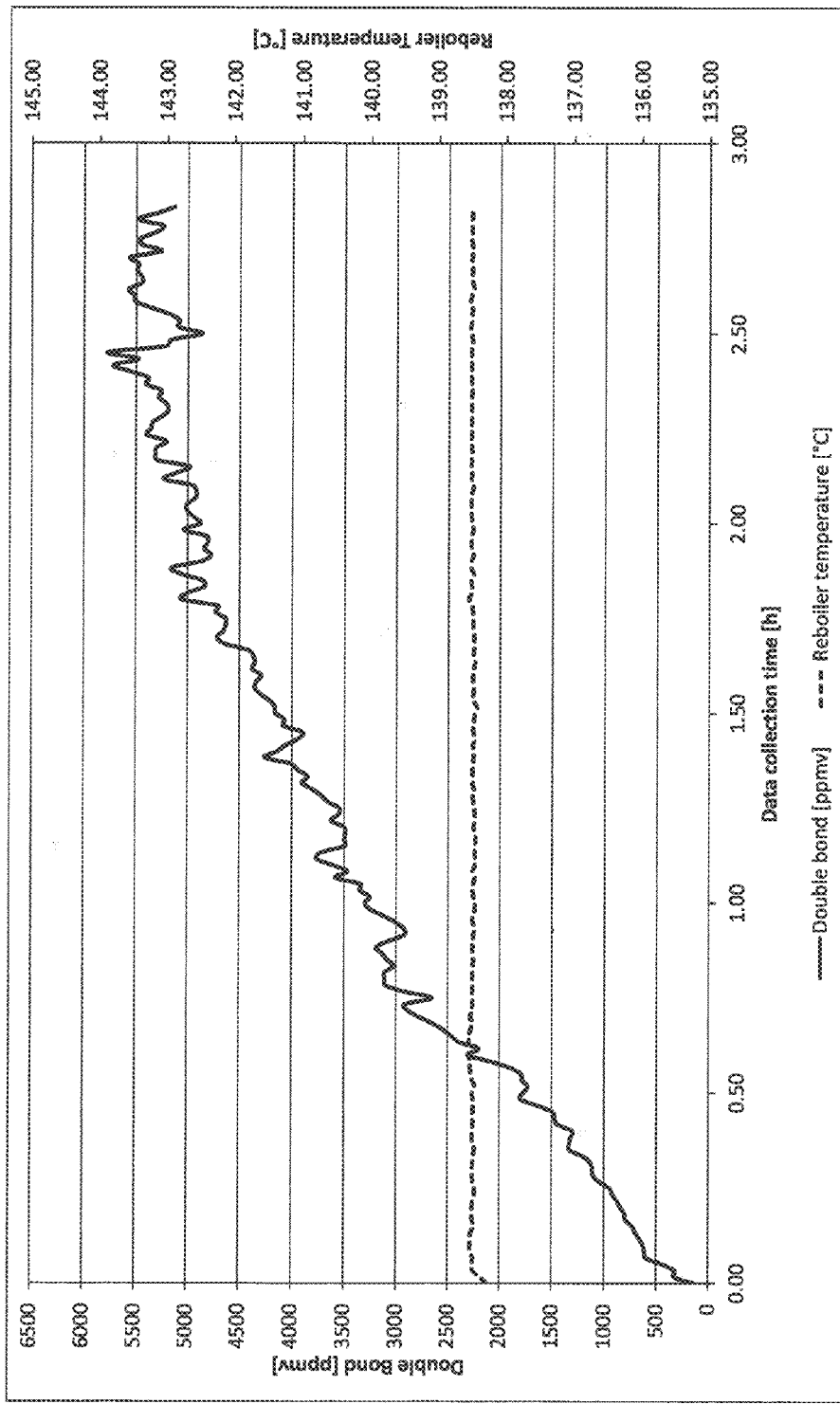
FIG. 7 graphs the continuous conversion of 3-hydroxy-3-methylpent-4-enoic acid to isoprene at elevated temperature and acidic pH in DSMZ media 81 in a reactive distillation unit operation with steam contact, showing the approach to steady state conversion alongside reboiler temperature.

DSMZ fermentation medium 81 was prepared with a five times concentrated trace metal solution and adjusted to pH=3.0 using phosphoric acid. The alkene precursor 3-hydroxy-3-methyl-pent-4-enoic acid was dissolved in the prepared fermentation media to a concentration of 9.5 [(g alkene precursor)/(kg total media)]. The reactive distillation unit was preheated to >120 [° C.] via pressure control. The media containing the alkene precursor was fed to the reactive distillation unit operation initially at 275 [g/h] to flush the recovery heat exchanger and establish media holdup in the reboiler (FIG. 6). The reboiler temperature was controlled at 139 [° C.] (FIG. 7) and the feed rate was decreased to approximately 160 [g/h], allowing the approach to steady state operation. The double bond concentration in the vapour product from the flash drum was analysed continuously for a period of approximately 2.5 [h] (FIG. 6 and FIG. 7), confirming the production of isoprene to high conversion as anticipated by Example 1. The results presented in FIG. 6 and FIG. 7 demonstrate that 3-hydroxy-3-methylpent-4-enoic acid can be converted in concentrated DSMZ-81 fermentation media to isoprene in a reactive distillation unit with steam contact at elevated temperature and acidic pH.

Example 3

Conversion of 3-hydroxy-3-methylbutyric Acid Dissolved in Fermentation Media to Isobutene Via Reactive Distillation with Steam Contact at Optimal pH A large scale laboratory reactive distillation unit with a temperature controlled flash drum was designed to operate at elevated pressure and temperature to demonstrate the continuous conversion of 3-hydroxyacid precursors to their respective alkene products. The flash drum was fitted with a knock-out after-cooler fed with chilled water at approximately 8 [° C.]. The flash drum was charged with water and temperature controlled to 10 [° C.]. The vapour product from the distillation unit was bubbled through the water charge and a constant flow of $N_2$ at 0.3 [SL/min] was introduced as carrier and stripping gas. The uncondensed vapour product from the flash drum was fed to a Raman Spectrometer, calibrated with a 0.5 [%] (v/v) 1,3-butadiene calibration cylinder as double bond reference gas to analyse for the concentration of double bonds in the vapour product from the flash drum.

Figure 8:
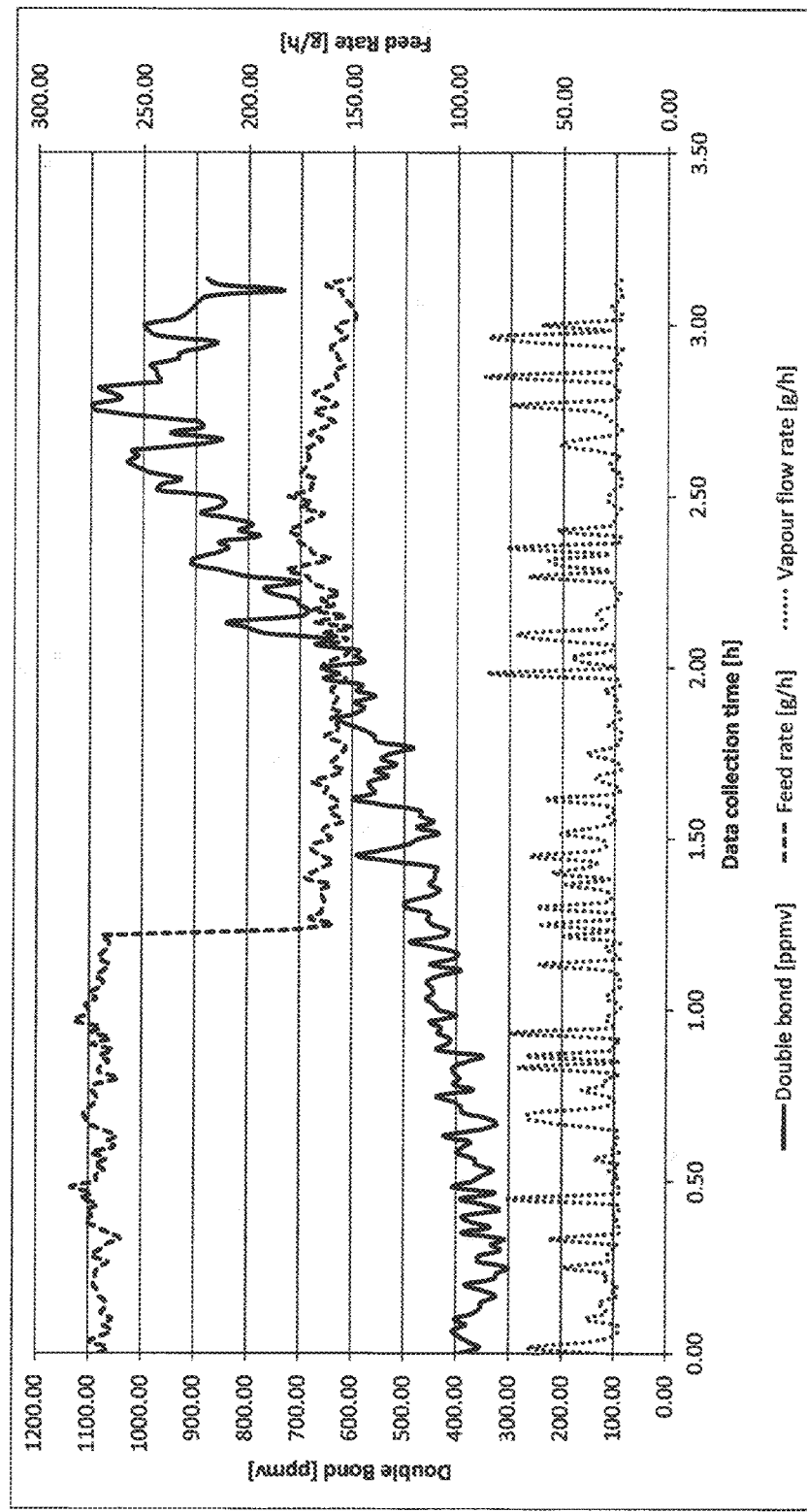
FIG. 8 graphs the continuous conversion of 3-hydroxy-3-methylbutyric acid to isobutene at elevated temperature and acidic pH in DSMZ media 81 in a reactive distillation unit operation with steam contact, showing the approach to steady state conversion alongside feed rate and total vapour product flow rate.
Figure 9:
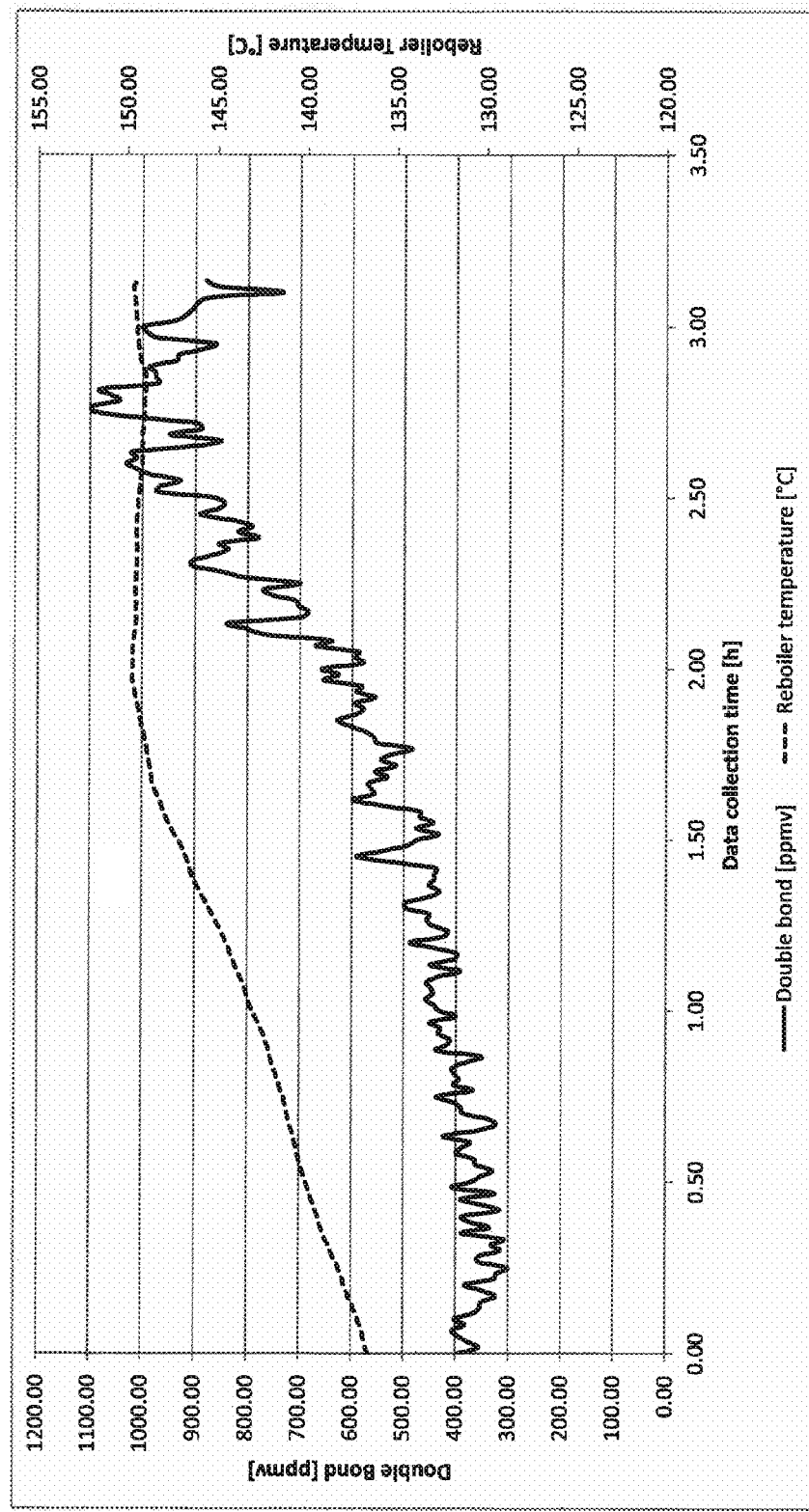
FIG. 9 graphs the continuous conversion of 3-hydroxy-3-methylbutyric acid to isobutene at elevated temperature and acidic pH in DSMZ media 81 in a reactive distillation unit operation with steam contact, showing the approach to steady state conversion alongside reboiler temperature.

DSMZ fermentation medium 81 was prepared with a five times concentrated trace metal solution and adjusted to pH=3.0 using phosphoric acid. The alkene precursor 3-hydroxy-3-methyl-butyric acid was dissolved in the prepared fermentation media to a concentration of 10.7 [(g alkene precursor)/(kg total media)]. The reactive distillation unit was preheated to >120 [° C.] via pressure control. The media containing the alkene precursor was fed to the reactive distillation unit operation initially at 275 [g/h] to flush the recovery heat exchanger and establish media holdup in the reboiler (FIG. 8). The reboiler temperature was increased from approximately 135 [DC] to a controlled temperature set point of 149 [° C.] (FIG. 9) and the feed rate was decreased to approximately 160 [g/h], allowing the approach to steady state operation. The double bond concentration in the vapour product from the flash drum was analysed continuously for a period of approximately 3 [h] (FIG. 8 and FIG. 9), confirming the production of isobutene to high conversion as anticipated by Example 1. The results presented in FIG. 8 and FIG. 9 demonstrate that 3-hydroxy-3-methylbutyric acid can be converted in concentrated DSMZ-81 fermentation media to isobutene in a reactive distillation unit with steam contact at elevated temperature and acidic pH.

What is claimed is:

1. A method for preparing an alkene product comprising:
   providing an alkene precursor, wherein the alkene precursor is a 3-hydroxyacid or an alcohol produced via fermentation in a fermentation media, wherein the 3-hydroxyacid is mevalonate, 3-methyl-3-hydroxybutyrate, 3-hydroxypent-4-enoate, 3-methyl-3-hydroxypent-4-enoate or 4-methyl-3-hydroxypent-4-enoate, and the alcohol is 3 methyl-2-buten-1-ol, 3-methyl-3-buten-1-ol, 3-buten-2-ol, 3-methyl-3-buten-2-ol or 2-methyl-3-buten-2-ol;
   distilling the alkene precursor using reactive distillation with steam contact; and
   forming at least one alkene product comprising at least one of isoprene, 1,3-butadiene and isobutene.

2. The method of claim 1, wherein the fermentation media comprises one or more of K, Na, P, Cl, N, Mg, Ca, and Fe.

3. The method of claim 2, wherein the fermentation media is adjusted to a pH of about 3.0 using an acid.

4. The method of claim 1, further comprising drying the at least one alkene product.

5. The method of claim 4, wherein the at least one alkene product is dried using an adsorbent.

6. The method of claim 5, wherein the adsorbent removes water from the at least one alkene product to a dew point of approximately −20° C.

7. The method of claim 5, wherein the adsorbent comprises a molecular sieve.

8. The method of claim 1, further comprising a polishing distillation step.

9. The method of claim 1, further comprising adding at least one alkene polymerization inhibitor to the reactive distillation.

10. The method of claim 1, further comprising separating the at least one alkene product.

11. The method of claim 10, wherein the at least one alkene product is separated by at least one of adsorption, membrane separation, and distillation.

12. The method of claim 10, further comprising condensing the at least one alkene product.

13. A method for preparing an alkene product comprising:
providing an alkene precursor, wherein the alkene precursor is a 3-hydroxyacid or an alcohol produced via fermentation in a fermentation media, wherein the 3-hydroxyacid is mevalonate, 3-methyl-3-hydroxybutyrate, 3-hydroxypent-4-enoate, 3-methyl-3-hydroxypent-4-enoate or 4-methyl-3-hydroxypent-4-enoate, and the alcohol is 3 methyl-2-buten-1-ol, 3-methyl-3-buten-1-ol, 3-buten-2-ol, 3-methyl-3-buten-2-ol or 2-methyl-3-buten-2-ol;
distilling the alkene precursor using reactive distillation with steam contact; and
converting the alkene precursor to an alkene by catalytic reaction, wherein the alkene comprises at least one of isoprene, 1,3-butadiene and isobutene.

14. The method of claim 13, wherein the fermentation media comprises one or more of K, Na, P, Cl, N, Mg, Ca, and Fe.

15. The method of claim 14, wherein the fermentation media is adjusted to a pH of about 3.0 using an acid.

16. The method of claim 13, wherein the catalytic reaction comprises reacting the alkene precursor with a dehydrating catalyst.

* * * * *